US012215374B2

(12) United States Patent
Dastoor

(10) Patent No.: US 12,215,374 B2
(45) Date of Patent: Feb. 4, 2025

(54) BIOSENSOR WITH POROUS WICKING LAYER

(71) Applicant: LIFE SCIENCE BIOSENSOR DIAGNOSTICS PTY LTD, Sydney (AU)

(72) Inventor: Paul Dastoor, Gosforth (AU)

(73) Assignee: The University of Newcastle, Callaghan (AU)

( * ) Notice: Subject to any disclaimer, the term of this patent is extended or adjusted under 35 U.S.C. 154(b) by 966 days.

(21) Appl. No.: 17/055,359

(22) PCT Filed: May 15, 2019

(86) PCT No.: PCT/AU2019/050458
§ 371 (c)(1),
(2) Date: Nov. 13, 2020

(87) PCT Pub. No.: WO2019/218011
PCT Pub. Date: Nov. 21, 2019

(65) Prior Publication Data
US 2021/0222223 A1 Jul. 22, 2021

(30) Foreign Application Priority Data
May 15, 2018 (AU) .............................. 2018901675

(51) Int. Cl.
*C12Q 1/00* (2006.01)
*C12Q 1/26* (2006.01)
(Continued)

(52) U.S. Cl.
CPC ............... *C12Q 1/006* (2013.01); *C12Q 1/26* (2013.01); *G01N 27/4145* (2013.01);
(Continued)

(58) Field of Classification Search
None
See application file for complete search history.

(56) References Cited

U.S. PATENT DOCUMENTS 5,215,887 A 6/1993 Saito
5,227,042 A 7/1993 Zawodzinski et al.
(Continued)

FOREIGN PATENT DOCUMENTS

JP S57127841 A 8/1982
JP S61155850 A 7/1986
(Continued)

OTHER PUBLICATIONS

Jung, Ho-Young; Kim, Jung Won; "Role of the glass transition temperature of Nafion 117 membrane in the preparation of the membrane electrode assembly in a direct methanol fuel cell (DMFC)" International Journal of Hydrogen Energy, 37, 12580-12585, 2012 (Year: 2012).*

(Continued)

*Primary Examiner* — David W Berke-Schlessel
(74) *Attorney, Agent, or Firm* — Scully, Scott, Murphy & Presser, P.C.

(57) ABSTRACT

The present invention relates to organic thin film sensors and the preparation and use thereof in sensing applications, and in particular in glucose sensing. The sensor is characterised by a layered structure comprising a porous wicking layer whose surface is configured to receive a liquid sample. An enzyme is disposed on or within the porous layer for facilitating the generation of a charge carrier from an analyte. A polymer layer in contact with the porous layer is connected to an ohmic conductor for applying a gate voltage to the polymer layer, the polymer layer being conductive to the charge carrier; and an organic semiconducting layer is connected to a source electrode and a drain electrode.

20 Claims, 4 Drawing Sheets

Layer 1
Electrodes,
ITO
(a)

Layer 2
Polymer
semiconductor,
P3HT
(b)

Layer 3
Gate electrode,
Nafion
(c)

Layer 4
Porous
membrane,
PAN
(d)

Layer 5
Enzyme,
GOX
(e)

(51) Int. Cl.
| | |
|---|---|
| *G01N 27/414* | (2006.01) |
| *H01L 51/00* | (2006.01) |
| *H01L 51/05* | (2006.01) |
| *H10K 10/46* | (2023.01) |
| *H10K 71/60* | (2023.01) |
| *H10K 85/10* | (2023.01) |
| *A61B 5/145* | (2006.01) |

(52) U.S. Cl.
CPC ......... *H10K 10/464* (2023.02); *H10K 10/471* (2023.02); *H10K 10/481* (2023.02); *H10K 10/488* (2023.02); *H10K 71/60* (2023.02); *H10K 85/141* (2023.02); *A61B 5/14507* (2013.01); *A61B 5/14532* (2013.01); *A61B 2560/0214* (2013.01)

(56) References Cited

U.S. PATENT DOCUMENTS

| | | | |
|---|---|---|---|
| 5,250,439 | A | 10/1993 | Musho et al. |
| 9,709,560 | B2 | 7/2017 | Horesh |
| 9,910,007 | B2 | 3/2018 | Fuerst et al. |
| 10,978,653 | B2 * | 4/2021 | Dastoor ................. C12Q 1/001 |
| 2006/0272942 | A1 | 12/2006 | Sirringhaus |
| 2007/0212860 | A1 | 9/2007 | Fujino et al. |
| 2010/0187107 | A1 | 7/2010 | Katsuki et al. |
| 2010/0224913 | A1 | 9/2010 | Chiang et al. |
| 2014/0013774 | A1 | 1/2014 | Grunwald et al. |
| 2014/0061728 | A1 | 3/2014 | Trivedi |
| 2014/0093902 | A1 | 4/2014 | Omenetto et al. |
| 2014/0098282 | A1 | 4/2014 | Yamada et al. |
| 2015/0037827 | A1 | 2/2015 | Dastoor et al. |
| 2017/0157583 | A1 | 6/2017 | Kulkarni et al. |
| 2017/0343508 | A1 | 11/2017 | Dastoor et al. |

FOREIGN PATENT DOCUMENTS

| | | | |
|---|---|---|---|
| JP | S61274682 | A | 12/1986 |
| JP | 2004105065 | A * | 4/2004 |
| JP | 2005062569 | A | 3/2005 |
| KR | 20070024661 | A | 3/2007 |
| TW | 201338230 | A | 9/2013 |
| WO | WO 2018/000012 | A1 | 1/2018 |

OTHER PUBLICATIONS

Lin, Hsiu-Li; et al; "Morphology Study of Nafion Membranes Prepared by Solutions Casting" Polymer Physics; 43, 3044-3057, 2005 (Year: 2005).*
Shan, Dan; et al; "A porous poly(acrylonitrile-co-acrylic acid) film-based glucose biosensor constructed by electrochemical entrapment" Analytical Biochemistry, 356, 215-221, 2006 (Year: 2006).*
Dang, Quoc-Khanh; et al; "Nafion membranes with a porous surface" Journal of Membrane Science, 460, 199-205, 2014 (Year: 2014).*
Bridge, KA; Higson, PJ; "Polyacrylonitrile Thin-Film Composite Membranes for the Optimization of a Whole Blood Glucose Sensor" Electroanalysis, 13, 191-198, 2001 (Year: 2001).*
Bartic C. et al., "Organic Thin-Films Transistors as Transducers for (Bio)Analytical Applications", Anal Bioanal Chem 384:354-365 (2006).
Darwis D. et al., "Novel Low Voltage and Solution Processable Organic Thin Film Transistors Based on Water Dispersed Polymer Semiconductor Nanoparticles", Journal of Colloid and Interface Science 401:65-69 (2013).
Elkington D. et al., "Printable Organic Thin Film Transistors for Glucose Detection Incorporating Inkjet-Printing of the Enzyme Recognition Element", Applied Physics Letters 106:263301 (2015).
Elkington D. et al., "Organic Thin-Film Transistor (OTFT)-Based Sensors", Electronics 3:234-254 (2014).
Fang A. et al., "A High-Performance Glucose Biosensor Based on Monomolecular Layer of Glucose Oxidase Covalently Immobilised on Indium-Tin Oxide Surface", Biosensors and Bioelectronics 19:43-49 (2003).
Holmes N.P. et al., "The Effect of Polymer Molecular Weight on P3HT:PCBM Nanoparticulate Organic Photovoltaic Device Performance", Solar Energy Materials & Solar Cells 128:369-377 (2014).
Liao C. et al., "Organic Semiconductors in Organic Thin-Film Transistor-Based Chemical and Biological Sensors", Polymer Reviews 53:352-406 (2013).
Lin P. et al., "Organic Thin-Film Transistors for Chemical and Biological Sensing", Advanced Material 24:34-51 (2012).
Liu J. et al., "Glucose Sensor Based on Organic Thin Film Transistor Using Glucose Oxidase and Conducting Polymer", Sensors and Actuators B 135:195-199 (2008).
Nikolou M. et al., "Applications of Poly (3,4-Ehtylenedioxythiophene) Doped With Poly(Styrene Sulfonic Acid) Transistors in Chemical and Biological Sensors", The Chemical Record 8:13-22 (2008).
Nilsson D. et al., "An All-Organic Sensor-Transistor Based on a Novel Electrochemical Transducer Concept Printed Electrochemical Sensors on Paper", Sensors and Actuators B 86(2-3): 193-197 (Sep. 2002).
Roberts M.E. et al., "Water-Stable Organic Transistors and Their Application in Chemical and Biological Sensors", PNAS 105(34): 12134-12139 (Aug. 26, 2008).
Sirois K. et al., "Hygroscopic Insulator Organic Field-Effect Transistor for Biosensing Applications", Abstract for presentation at Australian Institute of Physics 17th National Congress (2006).
Soldatkin A.P. et al., "Glucose-Sensitive Field-Effect Transistor With Additional Nafion Membrane-Reduction of Influence of Buffer Capacity on the Sensor Response and Extension of its Dynamic Range", Anal. Chim. Acta 283:695-701 (Nov. 1993).
Yan H. et al., "A High-Mobility Electron-Transporting Polymer for Printed Transistors", Nature 457(5):679-686 (2009).
Yao H. et al., "A Contact Lens With Embedded Sensor for Monitoring Tear Glucose Level", Biosensors and Bioelectronics 26:3290-3296 (2011).
Zhou X. et al., "Effects od Device Architecture on the Performance of Organic Thin Film Transistors", MRS Proceedings 1138, Cambridge University Press (2008).
International Search Report dated Jun. 13, 2019 issued in PCT/AU2019/050458.
Elkington, D., et al. "Detection of saliva-range glucose concentrations using organic thin-film transistors," Applied Physics Letters (2014), vol. 105, pp. 043303-1 to 043303-4.
Fryczkowska, Beata, et al. "Preparation and properties of composite PAN/PANI membranes," International Journal of Polymer Science (2017), vol. 2017.
Bae, Joonwon, et al., "Field-Effect Transistors Based on Organic and Carbon-Based Materials for Chemical and Biological Sensors," Current Organic Chemistry (2015), vol. 19, No. 12, pp. 1176-1190.
Torsi, Luisa et al., "Organic thin-film transistors as plastic analytical sensors," Analytical Chemistry (2005), pp. 380-A to 387-A.
Jiang, L., et al "Static and Dynamic modelling of organic thin-film transistors for circuit design", Microelectronics Journal (2016), pp. 1-7, 53.
Mabeck, J.T., et al., "Chemical and biological sensors based on organic thin film transistors", Analytical and Bioanalytical Chemistry, Jan. 2006, pp. 343-353, vol. 384, Issue 2.
Xue, H., et al., "A highly stable biosensor for phenols prepared by immobilizing polyphenol oxidase into polyaniline-polyacrylonitrile composite matrix", Talanta (2002), pp. 289-295, vol. 57.
Notice of Preliminary Rejection received in Korean Application No. 10-2020-7035946 dated Aug. 20, 2024, 21 pages.

* cited by examiner

BIOSENSOR WITH POROUS WICKING LAYER

FIELD OF THE INVENTION

The present invention relates to organic thin film sensors and the preparation and use thereof in sensing applications, and in particular in glucose sensing applications.

BACKGROUND OF THE INVENTION

The development of organic thin film transistors (OTFTs) sensors has grown rapidly in recent years motivated primarily by the unique physical properties of polymer devices, including their flexibility and ability to be fabricated using low-cost, solution-based techniques. Work on developing OTFTs for new and existing applications has focussed on two main areas. First, there have been systematic improvements in the materials and fabrication processes which have led to an improvement in the conventional performance parameters of organic devices making them comparable to their inorganic counterparts. Second, improvements in film morphology of the organic semiconducting layer have been made with the goal of eliminating electron and/or hole traps and enhancing free carrier transport in the polymer semiconducting materials. Progress has also been made in developing high capacitance organic dielectric layers and large improvements in OTFT performance have been reported. The inherent compatibility of organic materials with biological molecules makes OTFTs suitable for use in bio sensing applications.

The present inventors have successfully fabricated an OTFT device that is capable of detecting analyte levels across a broad range of concentrations and which is straightforward and relatively cheap to manufacture. The device may open the way for a commercially viable glucose sensor that allows blood glucose concentration to be estimated by detecting the level of glucose in saliva as opposed to blood. Such a device may obviate the need for diabetic patients to obtain a blood sample when determining their blood glucose level. The device may also open the way for sensing of other analytes in a similar fashion.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

SUMMARY OF THE INVENTION

In a first aspect of the invention there is provided an organic thin film transistor based sensor for detecting the presence of an analyte in a liquid sample, the sensor including:

- a porous wicking layer having a first surface and a second surface, wherein the first surface is configured to receive a liquid sample;
- an enzyme disposed on or within the porous layer, the enzyme for facilitating the generation of a charge carrier from an analyte;
- a polymer gating layer in contact with the second surface of the porous layer, and configured to be connected to an ohmic conductor for applying a gate voltage to the polymer gating layer, the polymer gating layer being conductive to the charge carrier; and
- an organic semiconducting layer configured to be connected to a source electrode and a drain electrode.

In an embodiment, the sensor further includes an ohmic conductor in contact with the polymer layer configured to apply a gate voltage to the polymer gating layer.

In an embodiment, the organic semiconducting layer is connected to and between a source electrode and a drain electrode.

In an embodiment, the porous layer has a thickness of from about 50 nm up to about 500 μm. Preferably, the thickness is up to 200 μm. More preferably, the thickness is up to 100 μm. Even more preferably, the thickness is up to 80 μm. Most preferably, the thickness is up to 60 μm. Alternatively, or additionally, the thickness is from 500 nm. More preferably the thickness is from 1 μm. Even more preferably, the thickness is from 20 μm. Most preferably, the thickness is from 40 μm. In a preferred form, the thickness is about 50 μm.

In an embodiment, the porous layer is formed from a material such that the contact angle of the liquid, preferably biofluid, more preferably diluted saliva, or undiluted saliva or unprocessed saliva ('neat saliva') on the first surface of the porous layer is 60° or less. Preferably, the contact angle is 50° or less. More preferably, the contact angle is 45° or less. Even more preferably, the contact angle is 40° or less. Most preferably, the contact angle is 38° or less.

In an embodiment, the porous layer includes a plurality of pores having a pore size of from 50 nm up to 2000 nm. Preferably, the pore size is up to 1600 nm. More preferably, the pore size is up to 1200 nm. Most preferably, the pore size is up to 1000 nm. Alternatively, or additionally, the pore size is from 80 nm. More preferably the pore size is from 100 nm. Most preferably, the pore size is from 150 nm.

In an embodiment the porous layer has a void ratio of from about 30% up to about 95%. Preferably the void ratio is up to about 90%. Alternatively, or additionally, the void ratio is from about 35%. Preferably, the void ratio is from about 40%. More preferably, the void ratio is from about 45%. Most preferably, the void ratio is from about 50%.

It will be appreciated that a range of different porous materials may be used to form the porous layer, such as a porous ceramic material, a porous metal, a porous layer formed from a protein fibre, or a porous polymer layer. In preferred forms of the invention, the porous layer is a porous polymer layer. The porous polymer layer may be a layer of a homopolymer, a copolymer, or a polymer blend.

In certain forms, the porous polymer layer includes, consists of, or consists essentially of a porous polymer, the enzyme, and optionally one or more additives selected from the group consisting of an elastomer, a stabiliser, or a surfactant.

In forms of the invention where the porous layer is a porous polymer layer, it is preferred that the polymer layer is formed from a polymer that has a glass transition temperature of at least 50° C. More preferably, the glass transition temperature is at least 70° C. Even more preferably, the glass transition temperature is at least 80° C. Still more preferably, the glass transition temperature is at least 90° C. Most preferably, the glass transition temperature is about 95° C.

In forms of the invention where the porous layer is a porous polymer layer, it is preferred that the porous polymer layer is formed from a polymer that is soluble in an organic solvent. Preferably, the polymer is soluble in a polar aprotic solvent, such as dimethyl sulfoxide.

In forms of the invention where the porous layer is a porous polymer layer, it is preferred that the porous polymer layer is formed from a polymer that is formed from a one or more repeating monomer units, wherein the one or more repeating monomer units do not include a halide atom. Preferably, the one or more repeating monomer units consist of C, N, O, and H atoms. More preferably, the one or more repeating monomer units consist of C, N, and H atoms.

In an embodiment, the porous wicking layer is a porous polyacrylonitrile (PAN) layer.

In one or more embodiments, the porous wicking layer is directly layered on a surface of the polymer gating layer.

In one or more embodiments, the polymer gating layer is directly layered on a surface of the organic semiconducting layer.

In one or more embodiments, the sensor also comprises a substrate layer. Preferably, at least the source electrode and drain electrode are disposed on the substrate. In at least one form, the source electrode, drain electrode and organic semiconductor are each in contact with the substrate. The substrate may be glass, or any other suitable substrate known to those skilled in the art, for example paper or a low-cost plastic, such as polyethylene terephthalate (PET).

In a preferred form of the invention, the analyte is glucose, and the enzyme is glucose oxidase.

In a second aspect of the invention, there is provided a method of forming the organic thin film transistor based sensor as defined according to the first aspect of the invention, the method including forming the porous wicking layer via a phase inversion method.

In one embodiment, the porous layer is formed in situ, on the surface of the polymer gating layer. In an alternative embodiment, the porous layer is first formed on a substrate that is separate from the organic thin film transistor based sensor and then subsequently removed from the substrate and applied to the surface of the polymer gating layer.

In a third aspect of the invention, there is provided a method of forming an organic thin film transistor based sensor for detecting the presence of an analyte in a liquid sample, the method including:
  providing a layered structure including at least an organic semiconducting layer configured to be connected to a source electrode and a drain electrode, and a polymer gating layer; and
  disposing a porous wicking layer on a surface of the polymer gating layer;
  wherein the porous wicking layer includes, or is treated to include an enzyme for facilitating the generation of a charge carrier from an analyte.

In one embodiment, the step of disposing a porous wicking layer on the surface of the polymer gating layer includes forming the porous wicking layer on the surface of the polymer gating layer via a phase inversion method.

In one or more embodiments, the phase inversion method includes:
  forming a wet film of a polymer solution on the surface of a substrate, the polymer solution including at least a polymer dissolved in a solvent; and
  applying a non-solvent to the wet film, the non-solvent being miscible with the solvent, to form a porous polymer membrane and to dissolve the solvent from pores of the porous polymer membrane.

In one form the substrate is a surface of the polymer gating layer. In an alternative form, the substrate is an inert layer that is separate from the organic thin film transistor based sensor, and the method further includes removing the porous wicking layer from the substrate prior to disposing the porous wicking layer on the surface of the polymer gating layer.

Further aspects of the present invention and further embodiments of the aspects described in the preceding paragraphs will become apparent from the following description, given by way of example and with reference to the accompanying drawings.

DETAILED DESCRIPTION OF THE EMBODIMENTS

In a first aspect of the invention there is provided an organic thin film transistor based sensor for detecting the presence of an analyte in a liquid sample, the sensor including:
  a porous wicking layer having a first surface and a second surface, wherein the first surface is configured to receive a liquid sample;
  an enzyme disposed on or within the porous layer, the enzyme for facilitating the generation of a charge carrier from an analyte;
  a polymer gating layer in contact with the second surface of the porous layer, the polymer gating layer configured to enable an ohmic conductor to connect to the polymer gating layer for applying a gate voltage to the polymer gating layer, the polymer gating layer being conductive to the charge carrier; and
  an organic semiconducting layer configured to be connected to a source electrode and a drain electrode.

Figure 1:
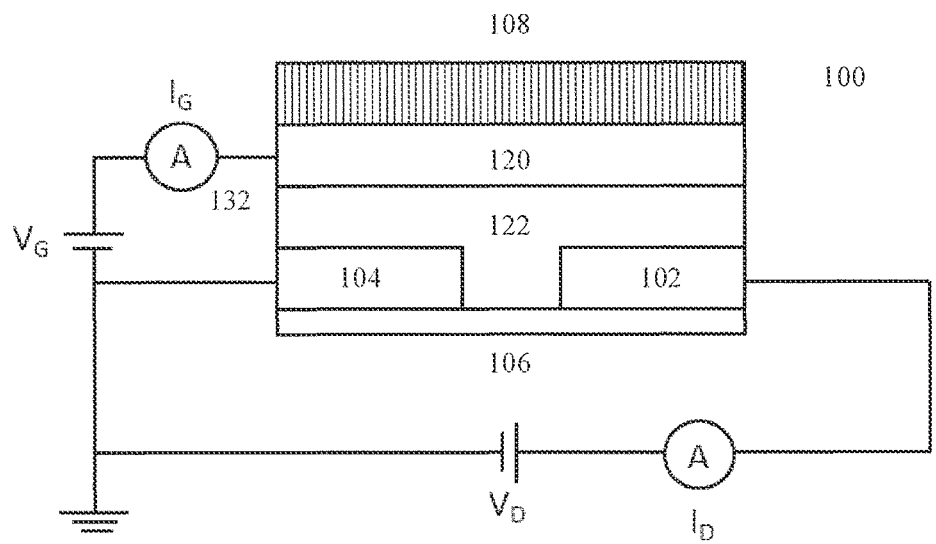
FIG. 1: Schematic illustrating the structure of a device in accordance with one embodiment of the invention.

An exemplary organic thin film transistor based sensor 100 in accordance with one embodiment of the invention is illustrated in FIG. 1, which provides a conceptual representation of the structure of the sensor 100. Sensor 100 includes a drain electrode 102 and source electrode 104 disposed on the surface of a substrate 106. The sensor includes a three-layered film structure that includes: a porous wicking layer 108, a polymer gating layer 120, and an organic semiconducting layer 122. The organic semiconducting layer 122 covers a portion of the drain and source electrodes, with the organic semiconducting layer 108 in contact with, and extending between the drain electrode 102 and the source electrode 104. The polymer gating layer 120 is disposed on a surface of the organic semiconducting layer 122. An ohmic conductor 132 is in contact with polymer gating layer 120 to enable a gate voltage to be applied to the polymer gating layer 120. A porous wicking layer 108 is disposed on the surface of the polymer gating layer 120. The surface of the porous wicking layer 108 is exposed to receive a fluid sample. An enzyme is disposed within and/or on the surface of the porous wicking layer 108. The porous wicking layer 100 is not located between gate and drain electrodes. The porous wicking layer 100 is not configured to enable an ohmic conductor to connect to the porous wicking layer.

The inventors have found that incorporation of a porous wicking layer including an enzyme into an organic thin film transistor is advantageous. This is for two primary reasons. Firstly, on depositing a liquid sample onto the surface of the porous wicking layer, the porous wicking layer exhibits a wicking effect which improves incorporation of a liquid sample into the device, this wicking effect has the potential to ensure delivery of a standard volume of liquid sample to within the device. Secondly, the wicking effect results in excellent wetting of the internal porous structure of the porous wicking layer which results in a high degree of exposure of an analyte within the liquid sample to the enzyme retained within the porous wicking layer. This is beneficial as it results in efficient generation of charge carriers within the device, and consequently the rapid detection of the analyte if present within the liquid sample.

The skilled person will appreciate that the porous wicking layer 108 may be formed from a range of different materials, including: porous ceramics, porous metals, porous protein fibres, or porous polymers. However, generally porous polymers are preferred for ease of sensor fabrication. Suitable polymers include, but are not limited to: polyacrylonitrile, polysulfone, polyethersulfone, polystyrene, polybutadiene, polyisoprene, polyimides, polyamides, and fluoropolymers. Typically the porous wicking layer is formed from a material that is not the same as the material that the polymer gating layer is formed from. Where the polymer gating layer is formed from Nafion, the porous wicking layer is not formed from Nafion. Preferably the porous wicking layer is not formed from Nafion.

Ideally the porous wicking layer 108 is formed from a material that has a low contact angle with the liquid of the liquid sample to ensure that the liquid sample is rapidly taken into the porous wicking layer 108 and that there is good wetting of pore surfaces of the porous wicking layer 108.

Preferably the porous wicking layer takes the form of a layer that enables the rapid formation of a droplet, preferably an aqueous droplet, more preferably a biological fluid droplet, more preferably a saliva droplet, such as a neat saliva droplet or a processed or diluted saliva droplet, on the porous wicking layer that has a low contact angle with the porous wicking layer.

Preferably the porous wicking layer is formed from a layer having a high degree of wettability by an aqueous droplet, more preferably a biological fluid droplet, more preferably a saliva droplet, more preferably a neat saliva droplet or a processed or diluted saliva droplet.

Notwithstanding the above, it is preferred that the porous wicking layer 108 is a porous poly(acrylonitrile) (PAN) layer. PAN has physical properties that make it particularly useful as the porous wicking layer 108. PAN is thermally stable with a glass transition temperature ($T_g$) of ~95° C. and melting temperature ($T_m$)>300° C. Given this, PAN exhibits good thermal stability, which is desirable in a sensor as this means that during typical use, the $T_g$ is unlikely to be exceeded. If the $T_g$ is exceeded, the porous structure may collapse. PAN also has high strength, a high modulus of elasticity, and a low density. Furthermore, from a fabrication point of view, PAN is soluble in dimethyl sulfoxide (DMSO) and can be used to prepare porous polymer membranes via the phase inversion technique-immersion precipitation.

In a preferred embodiment, the porous wicking layer has a sufficiently low surface energy to enable a body fluid, preferably saliva, preferably undiluted or otherwise unprocessed saliva, or processed saliva to rapidly wet and penetrate the porous wicking layer.

As discussed above, the porous wicking layer 108 includes an enzyme. The enzyme may be disposed on a surface of the porous wicking layer 108 and/or disposed throughout the porous wicking layer 108, such that the enzyme is exposed on pore surfaces within the porous wicking layer 108.

The enzyme is selected to facilitate generation of charge carriers when an analyte contacts the device. The charge carriers are typically electrons, anions, or cations (e.g. hydrogen ions/protons). The generation of the charge carriers may be further facilitated by the presence of an electric field. As will be described, these generated charge carriers can then contribute to electric current through the device. It will be recognised that a range of enzymes could be used for any one particular analyte. Further given the diversity of enzymes available, the device, by following the disclosure herein can be adapted or developed for detection of a range of analytes.

A particularly preferred class of enzyme is an oxidoreductase. An oxidoreductase for use in the device may act on any one of the following donor groups: the CH—OH group of donors (alcohol oxidoreductases), the aldehyde or oxo group of donors, the CH—CH group of donors (CH—CH oxidoreductases), the CH—$NH_2$ group of donors (amino acid oxidoreductases, monoamine oxidase), CH—NH group of donors, NADH or NADPH, other nitrogenous compounds as donors, a sulfur group of donors, a heme group of donors, diphenols and related substances as donors, peroxide as an acceptor (peroxidases), hydrogen as donors, single donors with incorporation of molecular oxygen (oxygenases), paired donors with incorporation of molecular oxygen, superoxide radicals as acceptors, CH or $CH_2$ groups, iron-sulfur proteins as donors, reduced flavodoxin as a donor, phosphorus or arsenic in donors, X—H and Y—H to form an X—Y bond, or oxidoreductases that oxidize metal ions.

The polymer gating layer 120 is disposed between the porous wicking layer 108 and the organic semiconducting layer 122. The function of polymer gating layer 120 is to facilitate transport of charge carriers generated in the porous wicking layer 108 from an analyte on application of a gate voltage. A range of different polymers may be used to form the polymer gating layer 120 depending on the nature of the analyte, enzyme, and/or charge carrier. In a preferred form, the charge carriers are protons (such as hydrogen ions) and the polymer gating layer 120 is proton conductive. Preferably the polymer layer has a conductivity to protons that is greater than a conductivity to protons of the organic semiconductor layer 122. The conductivity may be due to permeability of the polymer gating layer 120 to charge carriers, such as where conduction occurs via migration of the charge carriers; alternatively, conduction may occur via another mechanism, such as the Grotthuss mechanism. Where a charge carrier is a proton, or is an electron, the polymer gating layer may be proton conductive or electron conductive.

In preferred forms of the invention, the polymer gating layer 120 comprises, consists, or consists essentially of a sulfonated tetrafluoroethylene-based fluoropolymer-copolymer, for example a copolymer comprising a tetrafluoroethylene backbone and perfluoroalkyl ether groups terminated with sulfonate groups. More preferably, the sulfonated tetrafluoroethylene-based fluoropolymer-copolymer is a copolymer of tetrafluoroethylene and perfluoro-3,6-dioxa-4-methyl-7-octene-sulfonic acid. An example of a suitable polymer is tetrafluoroethylene-perfluoro-3,6-dioxa-4-methyl-7-octenesulfonic acid copolymer (commonly referred to as Nafion).

In preferred forms of the invention the polymer gating layer has a thickness in the range of from about 50 nm to about 5 μm. It is preferred that the thickness is from about 200 to about 800 nm.

The organic semiconducting layer 122 is configured to enable flow of electrical current between the source electrode and the drain electrode as a result of the generation of these charge carriers.

The organic semiconducting layer 122 includes one or more organic compounds. Any organic compound having semiconducting properties is suitable for use. However, it is preferred that the one or more organic compounds are selected from the group consisting of: polyacetylenes, porphyrins, phthalocyanins, fullerenes, polyparaphenylenes, polyphenylenevinylenes, polyfluorenes, polythiophenes, polypyrroles, polypyridines, polycarbazoles, polypyridinevinylenes, polyarylvinylenes, poly (p-phenylmethylvinylenes), including derivatives and co-polymers thereof, and further including combinations thereof. More preferably, the one or more organic compounds are selected from the group consisting of: poly(9,9-dioctylfluorene-2,7-diyl-co-bis-N,N-(4-butylphenyl)-bis-N, N-phenyl-1,4-phenylenediamine), poly(9,9-dioctylfluorene-2,7-diyl-co-benzothiadiazole), poly(3-hexylthiophene), (6,6)-phenyl-$C_{61}$-butyric acid methyl ester, poly(2-methoxy-5-(2'-ethyl-hexyloxy)-1,4-phenylene vinylene), and combinations thereof. Most preferably, the semiconducting layer includes, consists of, or consists essentially of P3HT.

In preferred forms of the invention, the organic semiconducting layer has a layer thickness of from 20 nm up to 500 nm. Preferably, the layer thickness is up to 350 nm. More preferably, the layer thickness is up to 200 nm. Most preferably, the layer thickness is up to 150 nm. Alternatively, or additionally, the layer thickness is from 40 nm. More preferably the layer thickness is from 60 nm. Most preferably, the layer thickness is from 70 nm.

The use of the sensor 100 will now be described below in relation to a preferred embodiment in which the sensor 100 is for detecting the presence of glucose in a saliva sample.

In use, a gate voltage $V_G$ and a drain voltage VD are applied to the sensor 100 (the voltages being with respect to the source electrode 104, as shown in FIG. 1), and a liquid sample comprising glucose, for example a bodily fluid such as saliva, is contacted with the porous wicking layer 108. The liquid sample is wicked into the internal porous structure of the porous wicking layer, where glucose in the liquid sample comes into contact with glucose oxidase enzyme (GOX) that is present within the porous wicking layer. The glucose is degraded via an enzymatic reaction with GOX thereby producing $H_2O_2$. The gate voltage $V_G$ and drain voltage $V_D$ provide a sufficiently strong electric field to liberate $H^+$ from $H_2O_2$, but not strong enough to cause electrolysis of water, as electrolysis of water may lead to a decrease in the signal-to-noise ratio of the sensor. Typically, the gate voltage and drain voltage applied are between about 0 V and −2 V, e.g. about −1 V.

The $H^+$ ions are conducted from the porous wicking layer 108 though the polymer gating layer 120 (e.g. Nafion) to the organic semiconducting layer. This results in doping of the semiconductor, and consequentially, current between the drain and the source electrodes. Without wishing to be bound by theory, the inventors are of the view that the gate potential controls the doping and de-doping of the semiconducting compound(s) via ion migration from the site of ion generation to the active channel in the organic semiconductor. Thus, the increase in $H^+$ ions results in an increase in drain current, such that a relationship is established between the amount of glucose present in the sample and the magnitude of the drain current. The drain current is then measured which provides an indication of the presence and concentration of glucose within the saliva sample.

The gate voltage $V_G$ and drain voltage $V_D$ provide a sufficiently strong electric field to liberate $H^+$ from $H_2O_2$, but not enough to cause electrolysis of water, as electrolysis of water may lead to a decrease in the signal-to-noise ratio of the sensor. In at least one embodiment, the gate voltage and drain voltage applied are between about 0 V and −2 V, e.g. about −1 V.

Figure 2:
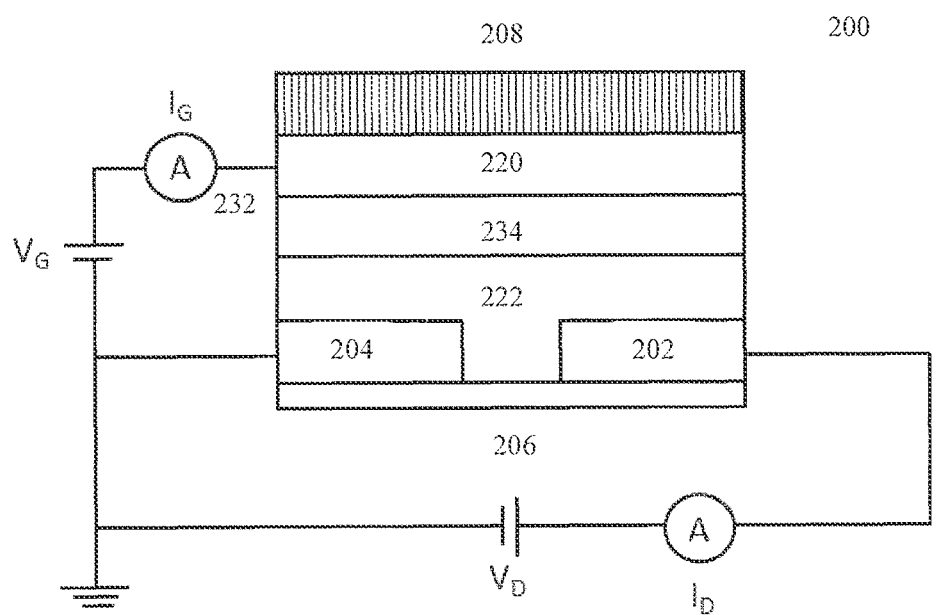
FIG. 2: Schematic illustrating the structure of a device in accordance with one embodiment of the invention.

In an alternative form of the invention, as illustrated in FIG. 2, the sensor 200 is similar to sensor 100 of FIG. 1, but further comprises a dielectric layer 234 between and in contact with polymer gating layer 220 and organic semiconductor layer 222.

The dielectric layer 234 comprises, consists of, or consists essentially of an organic dielectric material. Preferably, the organic dielectric material has a conductivity to protons that is greater than the conductivity of organic semiconductor layer 222. Preferably the organic dielectric material is a hygroscopic insulator, such as for example polyvinyl phenols. More specifically, the dielectric layer may comprise, consist of, or consist essentially of, poly(4-vinylphenol).

Alternative dielectric materials that may be used in the devices will be readily apparent to those skilled in the art. Non-limiting examples include polyimide and poly(methyl methacrylate) (PMMA). In alternative embodiments the dielectric layer may comprise a doped dielectric material, for example lithium perchlorate doped poly(4-vinylpyridine).

EXAMPLE

Fabrication of the Device

Pre-patterned ITO-on-glass substrates (15 Ω□$^{-1}$ ITO, Xin Yan Technology) were used as the substrate and electrodes of the devices. Poly-3-hexylthiophene (P3HT) (MW ~20 000) was dissolved in CHCl$_3$ (Sigma-Aldrich) at various concentrations and sonicated for ~1 hour or until the material was entirely dissolved. Poly-4-vinylphenol (PVP) (Sigma-Aldrich) was dissolved in ethanol (Sigma-Aldrich) at a concentration of 80 mg mL$^{-1}$ and sonicated for ~1 hour or until the material was entirely dissolved. Nafion solution (5% by weight in lower aliphatic alcohols and water, Sigma-Aldrich) was used as received.

The pre-patterned ITO-on-glass substrates were cleaned with methanol and purified water. P3HT solution in CHCl$_3$ was spin-coated onto the substrates at 2000 rpm for 60 seconds. P3HT solutions of 5 mg mL$^{-1}$, 10 mg mL$^{-1}$, 15 mg mL$^{-1}$, 20 mg mL$^{-1}$, and 40 mg mL$^{-1}$ were prepared, with average thicknesses of films spun from these concentrations of P3HT were 22 nm, 36 nm, 74 nm, 108 nm and 390 nm respectively. The P3HT layer was patterned and then left to dry for 15 minutes at 40° C. Nafion solution was first spin-coated at 500 rpm for 120 seconds.

While the devices exemplified herein do not include a dielectric layer, a dielectric layer may be included. A preferred dielelectric layer is a PVP layer. For devices including a PVP layer, PVP solution can be spun on top of the P3HT layer at 2000 rpm for 60 seconds to form a film of thickness ~400 nm, which can then patterned and dried. For PVP-containing devices, Nafion can then be drop-cast above the source-drain channel area and connected to the ITO gate pad of the substrate before being dried for approximately 30 minutes.

Porous polymer membranes can be fabricated using the phase inversion (immersion precipitation) technique. Firstly, a viscous solution of polyacrylonitrile (PAN) polymer in DMSO solvent is coated on a flat, rigid substrate, such as glass, to form a uniform 'wet' film. The 'wet' film can be coated by either spin coating, drop-casting or with the use of a printing technique such as slot-die coating. The 'wet' film is not a solid, dry film, it is a composite film, comprising a polymer network with liquid solvent molecules existing in the voids between polymer chains. The 'wet' film upon the rigid substrate is then submerged in water (the non-solvent), the porous polymer membrane forming as the DMSO solvent diffuses out of the polymer network into the surrounding water bath and the water diffuses into the polymer network. It is this solvent exchange with non-solvent that induces precipitation of the polymer. The selection of solvent and non-solvent is highly dependent on the chosen polymer, the solvent needs to be capable of dissolving the polymer whereas the non-solvent is one in which the polymer is insoluble. The solvent and non-solvent combination should be miscible, otherwise the solvent will not diffuse into the non-solvent and the porous polymer membrane will not form, instead remaining as a 'wet' solvent-containing film. The fabrication is a two-step process, it is during the second step that the 'wet' film transforms into a solid film. Once the solid film has been formed, it is processed into individual layers of the desired size and thickness and applied to the device as a porous wicking layer.

To incorporate GOX into the wicking layer, the GOX is cast on top of the wicking layer. The porosity of the wicking layer promotes the dispersion of the GOX throughout the wicking layer.

Testing of the Device

Figure 3:
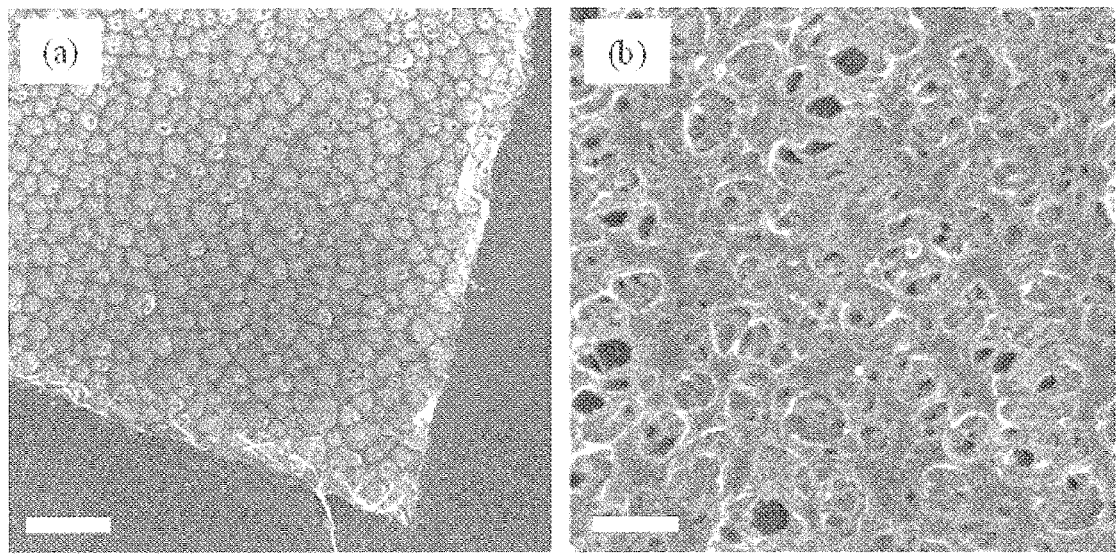
FIG. 3: Scanning electron micrographs (SEM) of poly (acrylonitrile) (PAN) porous membranes. The scale bar in (a) is 100 μm and the scale bar in (b) is 1 μm.

The porosity of PAN membranes prepared via the phase inversion technique were investigated using scanning electron microscopy (SEM) (see FIG. 3) on a Zeiss ZP FESEM operating at an accelerating voltage of 2 kV. DMSO was used as the solvent and water as the non-solvent in the membrane preparation process. SEM revealed PAN membrane pore size to be in the 200-800 nm size range.

Figure 4:
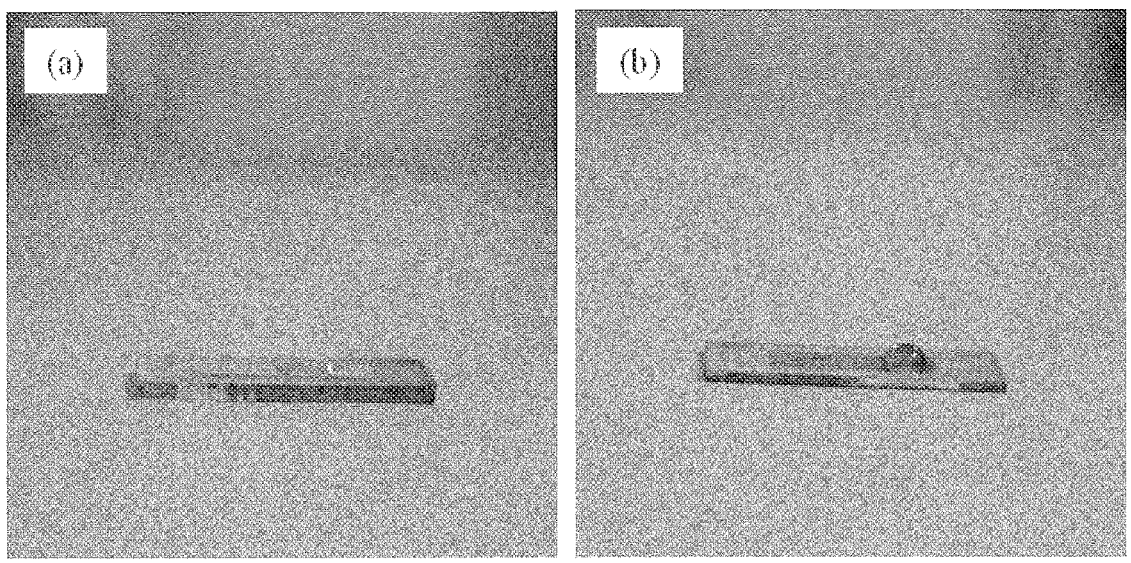
FIG. 4: Photograph depicting the contact angle of water on a glucose sensor (a) with poly(acrylonitrile) (PAN) and (b) without PAN.

To investigate the potential for wicking of PAN membranes, the contact angle of water on PAN compared to water on Nafion was measured. FIG. 4 presents photographs of water droplets on (a) PAN and (b) Nafion from which the contact angle was extracted. The contact angle of water on PAN was measured to be ~35°, this increased to ~70° on Nafion. The decreased contact angle of water on PAN indicates that PAN is a more hydrophilic surface than Nafion. This reduced contact angle on PAN is beneficial for a wicking effect, an excellent result for initial trials of this material.

X-ray photoelectron spectroscopy (XPS) was performed to probe any potential redistribution of Nafion throughout the PAN porous membranes following analyte addition. XPS spectra were collected by illuminating the samples with a non-monochromatic X-ray source (Omnivac) using Al Kα (1486.6 eV) radiation, and the photoemission collected by an SES2002 analyser (Scienta). The F 1s peak was utilised as a marker for Nafion as Nafion contains fluorine atoms attached to the carbon atoms of the polymer backbone whereas PAN only contains the elements carbon, nitrogen and hydrogen. Structures for (a) PAN and (b) Nafion are provided below:

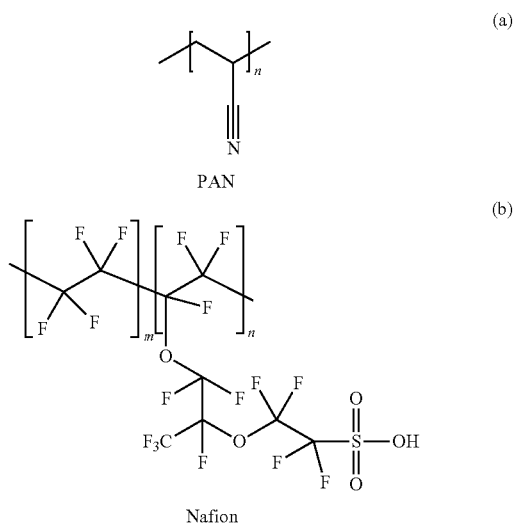

Figure 5:
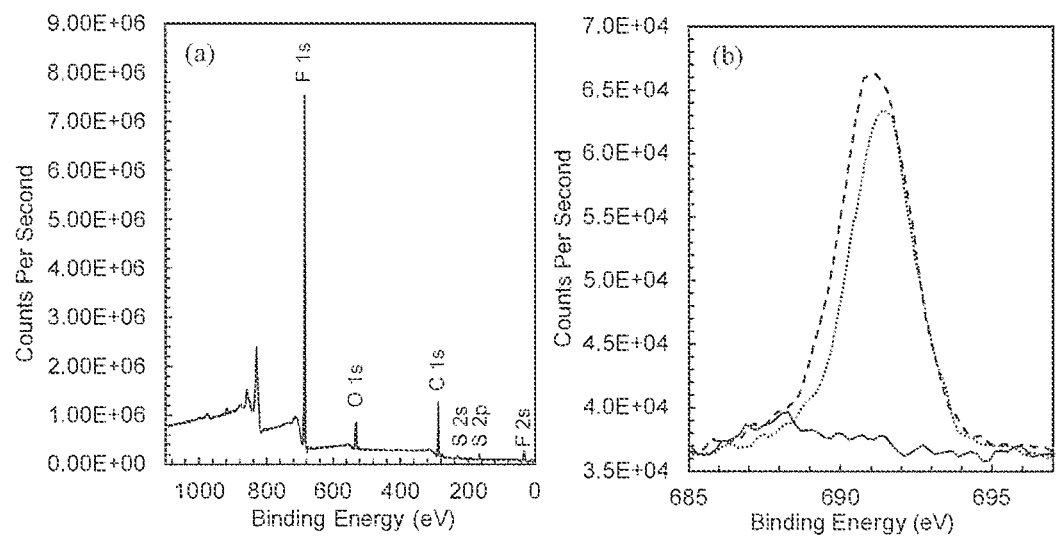
FIG. 5: (a) XPS survey scan of pristine Nafion film. (b) XPS region scans of pristine PAN membrane (solid line), Nafion/PAN bilayer (dashed line) and Nafion/PAN bilayer exposed to analyte solution (dotted line).

An XPS survey scan (FIG. 5(a)) of a pristine Nafion film identified the F 1s peak at a binding energy of 691 eV. XPS region scans were then performed of a pristine PAN membrane, a Nafion/PAN bilayer and a Nafion/PAN bilayer following exposure to analyte solution. The pristine PAN membrane had no F 1s peak (FIG. 5(b)). The Nafion/PAN bilayer XPS spectrum contains a peak for F 1s, the Nafion/PAN bilayer following exposure to analyte solution XPS spectrum also contains a peak for F 1s, and this peak is quite invariant compared to the Nafion/PAN bilayer indicating that the analyte solution does not cause solvation and redistribution of the underlying Nafion film. This is a positive result for the biosensors indicating that the Nafion film is quite robust.

Figure 6:
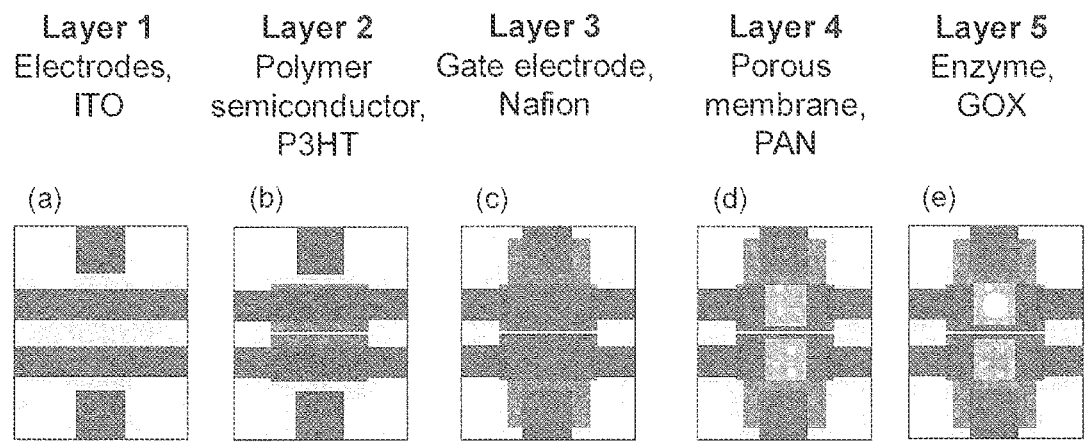
FIG. 6: Schematic depicting sensor device architecture incorporating porous poly(acrylonitrile) membranes, (a) layer 1, electrodes, ITO; (b) layer 2, polymer semiconductor, P3HT; (c) layer 3, gate electrode, Nafion; (d) layer 4, porous membrane, PAN; (e) layer 5, enzyme, GOX. Each substrate pictured contains two sensors.
Figure 7:
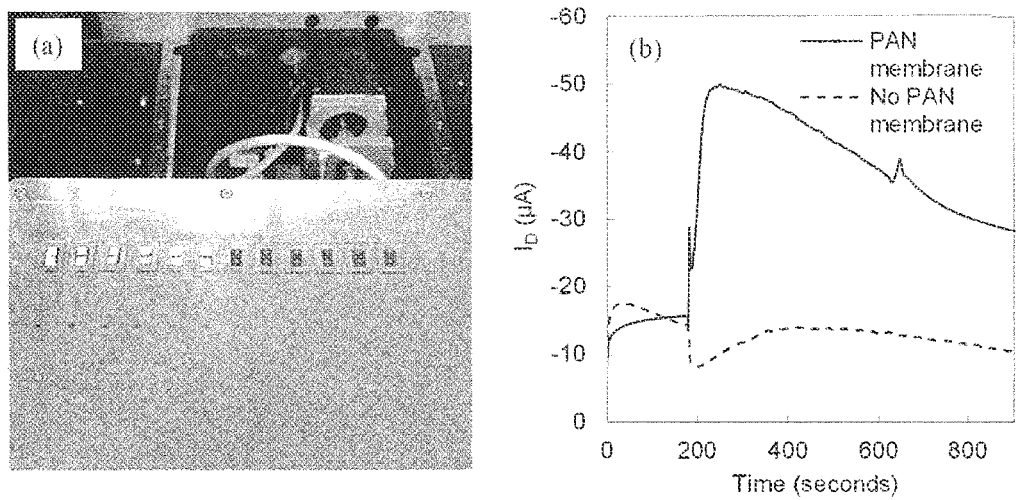
FIG. 7: (a) Photograph of sensors placed on inkjet printer platen following printing of GOX layer, the sensors on the left contain a PAN porous membrane and the sensors on the right do not contain a PAN porous membrane. (b) Sensor response to a 10 mM glucose solution added at t=180 s to a device containing a PAN membrane (solid line) and a device with no PAN membrane (dashed line).

Glucose sensors were fabricated with the architecture depicted in FIG. 6. Sensors with PAN and without PAN were fabricated and the GOX layer was inkjet printed with a Dimatix DMP 2831 inkjet printer with a 10 pL nozzle printing head (FIG. 7).

The sensors were exposed to glucose analyte solutions and the difference in response of sensors with and without PAN porous membranes was analysed. FIG. 7(b) presents representative plots of a sensor with PAN and a sensor without PAN following exposure to a 10 mM glucose solution. Here we observe an improvement in the drain current (ID) response time as well as the maximum current when we utilise porous PAN membranes. The rate of ID increase changes from 0.04 μA/s without PAN to 0.93 μA/s with PAN, and we observe a more than three-fold improvement in total ID for the PAN-containing sensor. The superior response time suggests that glucose is oxidised at a faster rate and/or the hydrogen peroxide is able to travel to the Nafion layer more quickly.

It will be understood that the invention disclosed and defined in this specification extends to all alternative combinations of two or more of the individual features mentioned or evident from the text or drawings. All of these different combinations constitute various alternative aspects of the invention.

The invention claimed is:

1. An organic thin film transistor based sensor for detecting the presence of an analyte in a hydrophilic liquid sample, the sensor including:
   a porous polymer wicking layer having a first surface and a second surface, wherein the first surface is configured to receive a liquid sample;
   an enzyme disposed on or within the porous polymer wicking layer, the enzyme for facilitating the generation of a charge carrier from an analyte;
   a polymer gating layer in contact with the second surface of the porous polymer wicking layer, and configured to be connected to an ohmic conductor for applying a gate voltage to the polymer gating layer, the polymer gating layer being conductive to the charge carrier; and
   an organic semiconducting layer configured to be connected to and between a source electrode and a drain electrode,
   wherein the porous polymer wicking layer is a different material than the polymer gating layer.

2. The sensor of claim 1, wherein the porous polymer wicking layer has a thickness of from 50 nm up to about 500 μm.

3. The sensor of claim 1, wherein a drop of the liquid on the first surface of the porous polymer wicking layer has a contact angle of 60° or less.

4. The sensor of claim 3, wherein the contact angle is 50° or less.

5. The sensor of claim 4, wherein the contact angle is 40° or less.

6. The sensor of claim 1, wherein the pore size is from 50 nm to 2000 nm.

7. The sensor of claim 6, wherein the pore size is from 100 nm to 1000 nm.

8. The sensor of claim 1, wherein the porous polymer wicking layer has a void ratio of from about 30% up to about 95%.

9. The sensor of claim 1, wherein the porous polymer wicking layer is formed from a polymer that has a glass transition temperature of at least 80° C.

10. The sensor of claim 9, wherein the glass transition temperature is at least 90° C.

11. The sensor of claim 1, wherein the porous polymer wicking layer is formed from a polymer that is soluble in dimethyl sulfoxide.

12. The sensor of claim 1, wherein the porous polymer wicking layer is formed from a polymer that is formed from a one or more repeating monomer units, wherein the one or more repeating monomer units do not include a halide atom.

13. The sensor of claim 12, wherein the one or more repeating monomer units consist of C, N, and H atoms.

14. The sensor of claim 1, wherein the porous polymer wicking layer is a porous polyacrylonitrile (PAN) layer.

15. The sensor of claim 1, wherein the enzyme is within the porous polymer wicking layer.

16. The sensor of claim 1, wherein the analyte is glucose and the enzyme is glucose oxidase.

17. The sensor of claim 1, wherein the polymer gating layer is a sulfonated tetrafluoroethylene-based fluoropolymer-copolymer.

18. The sensor of claim 17, wherein the polymer gating layer comprises tetrafluoroethylene-perfluoro-3,6-dioxa-4-methyl-7-octenesulfonic acid copolymer.

19. The sensor of claim 1, wherein the organic semiconducting layer includes one or more organic polymers selected from the group consisting of polyacetylenes, porphyrins, phthalocyanins, fullerenes, polyparaphenylenes, polyphenylenevinylenes, polyfluorenes, polythiophenes, polypyrroles, polypyridines, polycarbazoles, polypyridinevinylenes, polyarylvinylenes, poly(p-phenylmethylvinylenes).

20. The sensor of claim 1, wherein the organic semiconducting layer includes poly-3-hexylthiophene.

\* \* \* \* \*